United States Patent [19]

Lesher et al.

[11] 4,337,253

[45] Jun. 29, 1982

[54] 4,5-DIHYDRO-2-METHYL-6-(4-PYRIDINYL)-3(2H)-PYRIDAZINONE AND ITS USE AS A CARDIOTONIC

[75] Inventors: George Y. Lesher, Schodack; William B. Dickinson, Albany, both of N.Y.

[73] Assignee: Sterling Drug Inc., New York, N.Y.

[21] Appl. No.: 243,472

[22] Filed: Mar. 13, 1981

Related U.S. Application Data

[63] Continuation-in-part of Ser. No. 144,564, Apr. 28, 1980, abandoned.

[51] Int. Cl.$^3$ ............... C07D 401/04; C07D 401/06; A61K 31/50; C07D 215/50
[52] U.S. Cl. ............................... 424/250; 544/238; 544/131; 546/378; 546/315; 546/193; 546/281
[58] Field of Search ................... 544/238; 424/250

[56] References Cited

U.S. PATENT DOCUMENTS

| | | | |
|---|---|---|---|
| 3,746,712 | 7/1973 | Ross | 544/239 |
| 3,812,256 | 5/1974 | Curran | 544/239 |
| 3,822,260 | 7/1974 | Curran et al. | 544/239 |
| 4,004,012 | 1/1977 | Lesher et al. | 424/263 |
| 4,072,746 | 2/1978 | Lesher et al. | 424/263 |
| 4,107,315 | 8/1978 | Lesher et al. | 424/263 |
| 4,137,233 | 1/1979 | Lesher et al. | 424/257 |
| 4,199,586 | 4/1980 | Lesher et al. | 424/263 |

FOREIGN PATENT DOCUMENTS 54-19987 2/1979 Japan.

OTHER PUBLICATIONS

Nakao et al., Chem Abs. 90, 168635t (1978).
McEvoy et al., J. Med. Chem. 17, 281–286.
Haginiwa et al., [Yakugaku Zasshi 98 (1), 67–71 (1978); Chem. Abstrs. 88, 170,096v (1978)].
McEvoy and Allen [J. Org. Chem. 38, 4044–4048 (1973)].
Curran and Ross [J. Med. Chem. 17, 273–281 (1974)].
Albright, McEvoy and Moran [J. Heterocyclic Chem. 15, 881–892 (1978)].
McEvoy and Albright [J. Org. Chem. 44, 4597–4603 (1979)].
Leete et al. [J. Org. Chem. 37, 4465–4466 (1972)].

*Primary Examiner*—Mark L. Berch
*Attorney, Agent, or Firm*—Robert K. Bair; B. Woodrow Wyatt

[57] ABSTRACT

2-R-4,5-dihydro-4-R'-6-PY-3(2H)-pyridazinones (I) or salts thereof, which are useful as cardiotonics, where R is lower-alkyl or lower-hydroxyalkyl, R' is hydrogen or lower-alkyl, and PY is 4- or 3-pyridinyl or 4- or 3-pyridinyl having one or two lower-alkyl substituents, are prepared by reacting 4-oxo-4-PY-2-R'-butanenitrile with an N-R-hydrazine salt of a strong inorganic acid or organic sulfonic acid or by reacting a lower-alkyl 4-oxo-4-PY-2-R'-butanoate or lower-alkyl 4-(BN)-4-cyano-4-PY-2-R'-butanoate with N-R-hydrazine where BN is 4-morpholinyl, 1-piperidinyl or 1-pyrrolidinyl. Also shown are: (a) cardiotonic compositions and a method for increasing cardiac contractility using said compounds or salts where R is lower-alkyl (b) the use of I as intermediates in preparing the corresponding 2-R-4-R'-6-PY-3(2H)-pyridazinones; and, (c) the preparation of said lower-alkyl 4-(BN)-4-cyano-4-PY-2-R'-butanoates.

3 Claims, No Drawings

4,5-DIHYDRO-2-METHYL-6-(4-PYRIDINYL)-3(2H)-PYRIDAZINONE AND ITS USE AS A CARDIOTONIC

CROSS-REFERENCE TO RELATED APPLICATION

This application is a continuation-in-part of copending application Ser. No. 144,564, filed Apr. 28, 1980 and now abandoned.

4,5-Dihydro-6-(4-pyridinyl)-3-pyridazinol, tautomeric with 4,5-dihydro-6-(4-pyridinyl)-3(2H)-pyridazinone, is disclosed and claimed in copending application Ser. No. 71,064, filed Aug. 30, 1979 and now U.S. Pat. No. 4,298,609, issued Nov. 3, 1981. Also disclosed and claimed is the process which comprises reacting γ-oxo-γ-(4-pyridinyl)butyronitrile with a hydrazine salt of a strong inorganic or organic sulfonic acid to produce 4,5-dihydro-6-(4-pyridinyl)-3-pyridazinol. Also shown and claimed is the use of 4,5-dihydro-6-(4-pyridinyl)-3-pyridazinol in lowering blood pressure. 4,5-Dihydro-6-(4-pyridinyl)-3-pyridazinol or tautomeric 4,5-dihydro-6-(4-pyridinyl)-3(2H)-pyridazinone also is disclosed as an intermediate in copending U.S. patent applications Ser. No. 144,563 now U.S. Pat. No. 4,305,943 and 144,576, each filed Apr. 28, 1980, the latter now U.S. Pat. No. 4,304,777, to issue Dec. 8, 1981.

6-(4-Pyridinyl)-3-pyridazinol, tautomeric with 6-(4-pyridinyl)-3(2H)-pyridazinone and its preparation from 4,5-dihydro-6-(4-pyridinyl)-3-pyridazinol are disclosed and claimed in copending application Ser. No. 71,065, filed Aug. 30, 1979 and now abandoned in favor of its copending application Ser. No. 144,576 now U.S. Pat. No. 4,304,777. Also shown and claimed is the use of 6-(4-pyridinyl)-3-pyridazinol as a cardiotonic. 6-(4-Pyridinyl-3-pyridazinol or tautomeric 6-(4-pyridinyl)-3(2H)-pyridazinone also is disclosed as an intermediate in said copending U.S. patent applications Ser. Nos. 144,563 now U.S. Pat. No. 4,305,943 and Ser. No. 144,576, now U.S. Pat. No. 4,304,777.

Copending U.S. patent application Ser. No. 144,576 discloses and claims 2-R-6-PY-3(2H)-pyridazinones and their use as cardiotonics, where R is hydrogen, lower-alkyl or lower-hydroxyalkyl, and PY is 4- or 3-pyridinyl or 4- or 3-pyridinyl having one or two lower-alkyl substituents. Said 2-R-6-PY-3(2H)-pyridazinones also are disclosed as intermediates in said copending application Ser. No. 144,563.

The cardiotonic use of 4,5-dihydro-6-(4-pyridinyl)-3(2H)-pyridazinone is disclosed and claimed in applicants' copending application Ser. No. 245,086, filed Mar. 18, 1981 as a continuation-in-part application of its copending application Ser. No. 225,024, filed Jan. 14, 1981 and now abandoned.

BACKGROUND OF THE INVENTION (a) Field of the Invention

This invention relates to 2-substituted-4,5-dihydro-6-(pyridinyl)-3(2H)-pyridazinones, useful as cardiotonic agents, to their preparation, and to their use as cardiotonic agents.

(b) Description of the Prior Art

Haginiwa et al. [Yakugaku Zasshi 98 (1), 67-71 (1978); Chem. Abstrs. 88, 170,096v (1978)] reacted 3(2H)-pyridazinone with pyridine 1-oxide and platinized Pd-C catalyst to produce 6-(2-pyridinyl)-3(2H)-pyridazinone.

Yoshitomi Pharmaceutical Ind., Ltd. Japanese Patent Application Disclosure No. 19,987/79, published Feb. 15, 1979 and based on application No. 85,192/77, filed July 15, 1977, discloses, inter alia, the preparation of 4,5-dihydro-6-(4-pyridinyl)-3(2H)-pyridazinone by refluxing for two hours an ethanolic solution of 3-(isonicotinoyl)propanoic acid [same as γ-oxo-γ-(4-pyridinyl)-butyric acid] and hydrazine hydrate. 4,5-Dihydro-6-(4-pyridinyl)-3(2H)-pyridazinone and closely related 4,5-dihydro-6-(4- or 3- or 2-pyridinyl)-5-R-3(2H)-pyridazinones, where R is H or lower alkyl, are said (page 2 of English translation) to be "useful not only as medicines such as hypotensive and anti-thrombus agents because they have pharmacological actions such as hypotensive, blood platelet coagulation-inhibitory and membrane-stabilizing actions, but also as intermediates for the synthesis of such medicines".

McEvoy and Allen [J. Org. Chem. 38, 4044-48 (1973); J. Med. Chem. 17, 281-286 (1974)] show a method for preparing 3-(substituted-benzoyl)-3-substituted-alkanoic acids and their reaction with hydrazine to prepare 6-(substituted-phenyl)-5-substituted-4,5-dihydro-3(2H)-pyridazinones, hypotensive agents.

Curran and Ross [J. Med. Chem. 17, 273-281 (1974)] show the preparation of 6-phenyl-4,5-dihydro-3(2H)-pyridazinones, hypotensive agents, by refluxing the requisite 3-benzoylpropionic acid with hydrazine hydrate in ethanol.

Albright, McEvoy and Moran [J. Heterocyclic Chem. 15, 881-892 (1978)] show the use of α-(substituted-phenyl)-4-morpholineacetonitriles in 1,4-additions to ethyl acrylate, ethyl crotonate, methyl α-methylacrylate, acrylonitrile, methylacrylonitrile, crotononitrile and cinnamonitrile to produce 4-cyano-4-(4-morpholinyl)-4-(substituted-phenyl)-butanenitriles and butanoic acid esters, and their conversion by reaction with hydrazine to 6-(substituted-phenyl)-4,5-dihydro-3(2H)-pyridazinones and, in turn, their dehydrogenation by reaction with bromine to produce 6-(substituted-phenyl)-3-(2H)-pyridazinones optionally bearing methyl at the 4- or 5-position of the pyridazinone ring.

McEvoy and Albright [J. Org. Chem. 44, 4597-4603 (1979)] show inter alia, the reaction of 2-cyano-2-(4- or 3-pyridinyl)-2-(4-morpholinyl) ethanenitrile with acrylonitrile or ethyl acrylate to produce respectively ethyl 4-cyano-4-(4- or 3-pyridinyl)-4-(4-morpholinyl)butanoate or 4-cyano-4-(4- or 3-pyridinyl)-4-(4-morpholinyl)-butanenitrile.

Leete et al. [J. Org. Chem. 37, 4465-6 (1972)] shows the reaction of 2-(3-pyridinyl)-2-(4-morpholinyl)ethanenitrile with acrylonitrile to produce 4-cyano-4-(3-pyridinyl)-4-(4-morpholinyl)butanenitrile and its conversion by heating it with acetic acid, water and tetrahydrofuran to 4-oxo-4-(3-pyridinyl)butanenitrile.

SUMMARY OF THE INVENTION

In a composition of matter aspect, the invention resides in 2-R-4,5-dihydro-4-R'-6-PY-3(2H)-pyridazinones (I) or pharmaceutically-acceptable acid-addition salts thereof, where R, R' and PY are defined hereinbelow.

In a process aspect the invention comprises reacting 2-R'-4-oxo-4-PY-butanenitrile, lower-alkyl 2-R'-4-oxo-4-PY-butanoate or lower-alkyl 2-R'-4-(BN)-4-cyano-4-PY-butanoate with N-R-hydrazine.

A composition aspect of the invention resides in a cardiotonic composition for increasing cardiac contractility, said composition comprising a pharmaceutically-acceptable inert carrier and, as the active component thereof, a cardiotonically-effective amount of a 2-R-4,5-dihydro-4-R'-6-PY-3(2H)-pyridazinone or pharmaceutically-acceptable acid-addition salt thereof, where R, R' and PY are defined hereinbelow.

In a method aspect, the invention resides in a method for increasing cardiac contractility in a patient requiring such treatment which comprises administering orally or parenterally in a solid or liquid dosage form to such patient a cardiotonically-effective amount of a 2-R-4,5-dihydro-4-R'-6-PY-3(2H)-pyridazinone or pharmaceutically-acceptable acid-addition salt thereof, where R, R' and PY are defined hereinbelow.

DETAILED DESCRIPTION INCLUSIVE OF PREFERRED EMBODIMENTS

In a composition of matter aspect the invention resides in 2-R-4,5-dihydro-4-R'-6-PY-3(2H)-pyridazinones having formula I

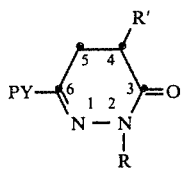

or pharmaceutically-acceptable acid-addition salt thereof, where PY is 4- or 3-pyridinyl or 4- or 3-pyridinyl having one or two lower-alkyl substituents, R is lower-alkyl or lower-hydroxyalkyl and R' is hydrogen or methyl. These compounds where R is lower-alkyl are useful as cardiotonic agents, as determined by standard cardiotonic evaluation procedures. All of the compounds of formula I also are useful as intermediates in the preparation of 2-R-6-PY-3(2H)-pyridazinones, cardiotonic agents, as disclosed and claimed in said copending application Ser. No. 144,576 now U.S. Pat. No. 4,304,777. Preferred embodiments are those where PY is 4-pyridinyl or 3-pyridinyl, R is methyl or ethyl, and R' is hydrogen.

In a process aspect the invention resides in the process of producing 2-R-4,5-dihydro-4-R'-6-PY-3(2H)-pyridazinones of Formula I which comprises reacting 2-R'-4-oxo-4-PY-butanenitrile, lower-alkyl 2-R'-4-oxo-4-PY-butanoate or lower-alkyl 2-R'-4-(BN)-4-cyano-4-PY-butanoate with N-R-hydrazine or its salt of a strong inorganic acid or organic sulfonic acid to produce 2-R-4,5-dihydro-4-R'-6-PY-3(2H)-pyridazinone, where PY, R' and R are defined as in formula I. In preferred embodiments, this process is run using 2-R'-4-oxo-4-PY-butanenitrile and N-R-hydrazine salt of a strong inorganic or a organic sulfonic acid, e.g., N-R-hydrazine sulfate or dihydrochloride, or using methyl 2-R'-4-oxo-4-PY-butanoate or methyl 2-R'-4-(4-morpholinyl)-4-cyano-4-(PY)-butanoate with N-R-hydrazine.

A composition aspect of the invention resides in the cardiotonic composition for increasing cardiac contractility, said composition comprising a pharmaceutically-acceptable inert carrier and, as the active component thereof, a cardiotonically-effective amount of a 2-R-4,5-dihydro-4-R'-6-PY-3(2H)-pyridazinone (formula I) or pharmaceutically-acceptable acid-addition salt thereof, where R is lower-alkyl, R' is hydrogen or lower-alkyl and, PY is defined as in formula I. Preferred embodiments are those where PY is 4-pyridinyl or 3-pyridinyl, R is methyl or ethyl, and R' is hydrogen.

In a method aspect, the invention resides in the method for increasing cardiac contractility in a patient requiring such treatment which comprises administering orally or parenterally in a solid or liquid dosage form to such patient a composition comprising a pharmaceutically-acceptable inert carrier and, as the active component thereof, a cardiotonically-effective amount of 2-R-4,5-dihydro-4-R'-6-PY-3(2H)-pyridazinone or pharmaceutically-acceptable acid-addition salt thereof, where R is lower-alkyl, and PY and R' are defined as in formula I. Preferred embodiments are those where PY is 4-pyridinyl or 3-pyridinyl, R is methyl or ethyl, and R' is hydrogen.

The term "lower-alkyl" as used herein, e.g., as one of the meanings for R or R' (formula I), or as a substituent for PY (formula I) means alkyl radicals having from one to six carbon atoms which can be arranged as straight or branched chains, illustrated by methyl, ethyl, n-propyl, isopropyl, n-butyl, 2-butyl, isobutyl, n-hexyl and the like.

The symbol PY as used here, e.g., as the 6-substituent in the compounds having formula I, means 4- or 3-pyridinyl or 4- or 3-pyridinyl having one or two "lower-alkyl" substituents, illustrated by 2-methyl-4-pyridinyl, 2,6-dimethyl-4-pyridinyl, 3-methyl-4-pyridinyl, 2-methyl-3-pyridinyl, 6-methyl-3-pyridinyl (alternatively named 2-methyl-5-pyridinyl), 2,3-dimethyl-4-pyridinyl, 2,6-dimethyl-4-pyridinyl, 2-ethyl-4-pyridinyl, 2-isopropyl-4-pyridinyl, 2-n-butyl-4-pyridinyl, 2-n-hexyl-4-pyridinyl, 2,6-diethyl-4-pyridinyl, 2,6-diethyl-3-pyridinyl, 2,6-diisopropyl-4-pyridinyl, 2,6-di-n-hexyl-4-pyridinyl, and the like.

The term "lower-hydroxyalkyl", as used herein, e.g., as one of the meanings for R in formula I, means hydroxyalkyl radicals having from two to six carbon atoms and having its hydroxy group and its free valence bond (or connecting linkage) on different carbon atoms which can be arranged as straight or branched chains, illustrated by 2-hydroxyethyl, 2-hydroxypropyl, 3-hydroxypropyl, 2-hydroxy-2-methylpropyl, 2-hydroxy-1,1-dimethylethyl, 4-hydroxybutyl, 5-hydroxyamyl, 6-hydroxyhexyl, and the like.

The compounds of the invention having formula I, are useful both in the free base form and in the form of acid-addition salts, and both forms are within the purview of the invention. The acid-addition salts are simply a more convenient form for use; and in practice, use of the salt form inherently amounts to use of the base form. The acids which can be used to prepare the acid-addition salt include preferably those which produce, when combined with the free base, pharmaceutically-acceptable salts, that is, salts whose anions are relatively innocuous to the animal organism in pharmaceutical doses of the salts, so that the beneficial cardiotonic properties inherent in the free base of the cardiotonically-active compounds (I) of the invention are not vitiated by side effects ascribable to the anions. In practicing the invention, it is convenient to use the free base form; however, appropriate pharmaceutically-acceptable salts within the scope of the invention are those derived from mineral acids such as hydrochloric acid, sulfuric acid, phosphoric acid and sulfamic acid; and organic acid such as acetic acid, citric acid, lactic acid, tartaric acid, methanesulfonic acid, ethanesulfonic acid, benzenesulfonic acid, p-toluenesulfonic acid, cyclohexylsulfamic acid, quinic acid, and the like, giving the hydrochloride, sulfate, phosphate, sulfamate, acetate, citrate, lactate, tartrate, methanesulfonate, ethanesulfonate, benzenesulfonate, p-toluenesulfonate, cyclohexylsulfamate and quinate, respectively.

The acid-addition salts of said basic compound are prepared either by dissolving the free base in aqueous or aqueous-alcohol solution or other suitable solvents containing the appropriate acid and isolating the salt by evaporating the solution, or by reacting the free base and acid in an organic solvent, in which case the salt separates directly or can be obtained by concentration of the solution.

Although pharmaceutically-acceptable salts of said basic compound are preferred, all acid-addition salts are within the scope of our invention. All acid-addition salts are useful as sources of the free base form even if the particular salt per se is desired only as an intermediate product as for example when the salt is formed only for purposes of purification or identification, or when it is used as an intermediate in preparing a pharmaceutically-acceptable salt by ion exchange procedures.

The molecular structures of formula I were assigned on the basis of evidence provided by infrared, nuclear magnetic resonance and mass spectra, and by the correspondence of the calculated and found values for the elemental analysis.

The manner of making and using the instant invention will now be generally described so as to enable a person skilled in the art of pharmaceutical chemistry to make and use the same, as follows.

The reaction of 2-R'-4-oxo-4-PY-butanenitrile with an N-R-hydrazine salt of a strong inorganic or organic sulfonic acid to produce 2-R-4,5-dihydro-4-R'-6-PY-3(2H)-pyridazinone is carried out by heating the reactants at about 65°–120° C. in a suitable solvent, preferably at about 80°–100° C. in a mixture of water and a lower alkanol. The reaction is preferably run by refluxing 2-R'-4-oxo-4-PY-butanenitrile with hydrazine sulfate in aqueous ethanol. Other N-R-hydrazine salts usable are N-R-hydrazine dihydrochloride, N-R-hydrazine dimethanesulfonate, and the like salts derived from phosphoric acid, ethanesulfonic acid, benzenesulfonic acid, and the like acids. Other lower-alkanols useful as solvents are methanol, n-propanol, 2-propanol, n-butanol, 2-butanol and 2-methyl-n-propanol. This reaction is illustrated below in Examples A-1 thru A-15.

The intermediate 2-R'-4-oxo-4-PY-butanenitriles are generally known compounds, e.g., Stetter et al. Chem. Ber. 107, 210 (1974), Leete et al. J. Org. Chem. 37, 4466 (1972) and Stetter et al. U.S. Pat. No. 4,014,889 (Mar. 29, 1977), and are prepared by generally known methods. Preparation of these compounds is illustrated below in Examples C-1 thru C-6.

The reaction of lower-alkyl 2-R'-4-oxo-4-PY-butanoate or lower-alkyl 2-R'-4-(BN)-4-cyano-4-PY-butanoate with N-R-hydrazine to produce 2-R-4,5-dihydro-4-R'-6-PY-3(2H)-pyridazinone is carried out by heating the reactants at about 65°–120° C. in a suitable solvent, preferably at about 80°–100° C. in a lower-alkanol. The reaction is preferably run by refluxing the reactants in ethanol. Other lower-alkanols suitable as solvents are methanol, n-butanol, 2-butanol and 2-methyl-n-propanol. This reaction is illustrated below in Examples A-16 through A-23.

The intermediate lower-alkyl 2-R'-4-oxo-4-PY-butanoates and/or corresponding acids are generally known compounds [Wada et al. J. Am. Chem. Soc. 76, 155 (1954)], which are readily obtained by hydrolysis of said generally known 2-R'-4-oxo-4-PY-butanenitriles and esterification of the resulting 2-R'-4-oxo-4-PY-butanoic acids.

The reaction of 2-(BN)-2-PY-ethanenitrile (III) with lower-alkyl 2-R'-2-propenoate (IV) to produce lower-alkyl 2-R'-4-(BN)-4-cyano-4-PY-butanoate (II) is carried out under anhydrous conditions by mixing the reactants at about 25° C. to 60° C., preferably about 30° C. to 50° C., in a suitable solvent in the presence of a basic condensing agent. The reaction is conveniently run by mixing the reactants at about 30° C. to 50° C. in dry tetrahydrofuran in the presence of an alkali hydroxide in methanol. Other suitable solvents are other lower-alkanols, e.g., ethanol or isopropyl alcohol, dimethylformamide, acetonitrile tetrahydrofuran, benzene and the like. Suitable basic condensing agents include alkali hydroxides, e.g., potassium or sodium hydroxide, alkali lower-alkoxides, e.g., sodium methoxide or potassium ethoxide, sodium hydride, and the like.

The intermediate 2-(BN)-2-PY-ethanenitriles (III) are generally known compounds, e.g., Janssen et al., J. Am. Pharm. Assoc., Sci. Ed., 44, 465–7 (1955), and are prepared by generally known methods. Preparation of these compounds is illustrated below in Examples E-1 through E-5.

The conversion of the intermediate 4,5-dihydro-2-R-4-R'-6-PY-3(2H)-pyridazinones by reaction with bromine to the corresponding 2-R-4-R'-6-PY-3(2H)-pyridazinones, the 2-R-4-R'-6-PY-3(2H)-pyridazinones produced by the conversion and the use of the latter where R' is hydrogen as cardiotonics are disclosed and claimed in said copending application Ser. No. 144,576 now U.S. Pat. No. 4,304,777. This conversion and products produced thereby are illustrated below in Examples B-1 through B-15 for compounds where R' is hydrogen and in Examples B-16 through B-23 for compounds where R' is methyl.

The following examples will further illustrate the invention without, however, limiting it thereto.

A.

4,5-DIHYDRO-2-R-4-R'-6-PY-3(2H)-PYRIDAZINONES

A-1.

4,5-Dihydro-2-methyl-6-(4-pyridinyl)-3(2H)-pyridazinone

To a stirred hot solution containing 25.6 g. of N-methylhydrazine dihydrochloride, 400 ml. of absolute ethanol and 70 ml. of water was added 32 g. of 4-oxo-4-(4-pyridinyl)butanenitrile and the resulting reaction mixture was refluxed overnight (about 15 hours). The solvent was distilled off in vacuo and the resulting solid was recrystallized from ethanol and dried in a vacuum oven at 65° C. overnight to yield 10.5 g. of 4,5-dihydro-2-methyl-6-(4-pyridinyl)-3(2H)pyridazinone as its monohydrochloride, m.p. 219°–225° C. with decomposition.

Acid-addition salts of 4,5-dihydro-2-methyl-6-(4-pyridinyl)-3(2H)-pyridazinone are conveniently prepared by adding to a mixture of 1 g. of 4,5-dihydro-2-methyl-6-(4-pyridinyl)-3(2H)-pyridazinone in about 20 ml. of aqueous methanol the appropriate acid, e.g., hydrochloric acid, methanesulfonic acid, sulfuric acid, to a pH of about 2 to 3, chilling the mixture after partial evaporation and collecting the precipitated salt, e.g., hydrochloride, methanesulfonate, sulfate, respectively. Also, the lactate or hydrochloride acid-addition salt of 4,5-dihydro-2-methyl-6-(4-pyridinyl)-3(2H)-pyridazinone is conveniently prepared in aqueous solution by adding to water with stirring molar equivalent quantities each of 4,5-dihydro-2-methyl-6-(4-pyridinyl)-3(2H)-pyridazinone and lactic acid or hydrochloric acid, respectively.

Following the procedure described in Example A-1 but using in place of N-methylhydrazine dihydrochloride a molar equivalent quantity of the appropriate N-R-hydrazine dihydrochloride or other salt of a strong inorganic acid or organic sulfonic acid, it is contemplated that there can be obtained the corresponding 4,5-dihydro-2-R-6-(4-pyridinyl)-3(2H)-pyridazinones (or salts thereof) of Examples A-2 thru A-10.

A-2. 2-Ethyl-4,5-dihydro-6-(4-pyridinyl)-3(2H)-pyridazinone.
A-3. 4,5-Dihydro-2-isopropyl-6-(4-pyridinyl)-3(2H)-pyridazinone.
A-4. 4,5-Dihydro-2-n-propyl-6-(4-pyridinyl)-3(2H)-pyridazinone.
A-5. 4,5-Dihydro-2-isobutyl-6-(4-pyridinyl)-3(2H)-pyridazinone.
A-6. 2-n-Hexyl-4,5-dihydro-6-(4-pyridinyl)-3(2H)-pyridazinone.
A-7. 2-(2-Hydroxyethyl)-4,5-dihydro-6-(4-pyridinyl)-3(2H)-pyridazinone, m.p. 142°-144° C.
A-8. 2-(2-Hydroxypropyl)-4,5-dihydro-6-(4-pyridinyl)-3(2H)-pyridazinone.
A-9. 2-(3-Hydroxypropyl)-4,5-dihydro-6-(4-pyridinyl)-3(2H)-pyridazinone.
A-10. 2-(4-Hydroxybutyl)-4,5-dihydro-6-(4-pyridinyl)-3(2H)-pyridazinone.

Following the procedure described in Example A-1 but using in place 4-oxo-4-(4-pyridinyl)butanenitile a molar equivalent quantity of the appropriate 4-oxo-4-PY-butanenitrile, it is contemplated that the 4,5-dihydro-6-PY-2-methyl-3(2H)-pyridazinones of Examples A-11 through A-15 can be obtained.

A-11. 4,5-Dihydro-2-methyl-6-(3-pyridinyl)-3(2H)-pyridazinone.
A-12. 4,5-Dihydro-2-methyl-6-(2-methyl-3-pyridinyl)-3(2H)-pyridazinone.
A-13. 4,5-Dihydro-2-methyl-6-(5-methyl-3-pyridinyl)-3(2H)-pyridazinone.
A-14. 2-Ethyl-6-(3-ethyl-4-pyridinyl)-4,5-dihydro-2-methyl-3(2H)-pyridazinone.
A-15. 4,5-Dihydro-2-methyl-6-(2,6-dimethyl-4-pyridinyl)-3(2H)-pyridazinone.

A-16. 4,5-Dihydro-2,4-dimethyl-6-(4-pyridinyl)-3(2H)-pyridazinone

A mixture containing 16 g. of methyl 4-cyano-2-methyl-4-(4-morpholinyl)-4-(4-pyridinyl)butanoate, 30 ml. of N-methylhydrazine and 220 ml. of absolute ethanol was refluxed with stirring for about seventeen hours. The ethanol was distilled off in vacuo and the remaining oily material was placed on a column of silica gel (7 cm. high and 15 cm. in diameter) in a large scintered glass funnel and eluted with a 50—50 mixture (by volume) of ether and n-hexane. Evaporation of the eluants containing the bulk of the product, as indicated by tlc analysis (CHCl₃: CH₃OH: i-C₃H₇NH₂/90%: 5%: 5% by volume), yielded solid product, which was recrystallized from ether-n-hexane and dried in vacuo at 50° C. to yield 3.0 g. of 4,5-dihydro-2,4-dimethyl-6-(4-pyridinyl)-3(2H)-pyridazinone, m.p. 71°-81° C.

Acid-addition salts of 4,5-dihydro-2,4-dimethyl-6-(4-pyridinyl)-3(2H)-pyridazinone are conveniently prepared by adding to a mixture of 1 g. of 4,5-dihydro-2,4-dimethyl-6-(4-pyridinyl)-3(2H)-pyridazinone in about 20 ml. of aqueous methanol the appropriate acid, e.g., hydrochloric acid, methanesulfonic acid, sulfuric acid, to a pH of about 2 to 3, chilling the mixture after partial evaporation and collecting the precipitated salt, e.g., hydrochloride, methanesulfonate, sulfate, respectively. Also, the lactate or hydrochloride acid-addition salt of 4,5-dihydro-2,4-dimethyl-6-(4-pyridinyl)-3(2H)-pyridazinone is conveniently prepared in aqueous solution by adding to water with stirring molar equivalent quantities each of 4,5-dihydro-2,4-dimethyl-6-(4-pyridinyl)-3(2H)-pyridazinone and lactic acid or hydrochloric acid, respectively.

Following the procedure described in Example A-16 but using in place of methyl 4-cyano-4-(4-morpholinyl)-4-(4-pyridinyl)-2-methylbutanoate and N-methylhydrazine corresponding molar equivalent quantities of the appropriate respective lower-alkyl 4-cyano-4-(BN)-4-PY-2-methylbutanoate and N-R-hydrazine, it is contemplated that the corresponding 4,5-dihydro-4-methyl-6-PY-2-R-3(2H)-pyridazinones of Examples A-17 through A-23 can be obtained.

A-17. 4,5-Dihydro-2,4-dimethyl-6-(3-pyridinyl)-3(2H)-pyridazinone.
A-18. 2-Ethyl-4,5-dihydro-4-methyl-6-(4-pyridinyl)-3(2H)-pyridazinone.
A-19. 4,5-Dihydro-4-methyl-2-n-propyl-6-(4-pyridinyl)-3(2H)-pyridazinone.
A-20. 4,5-Dihydro-2-isopropyl-4-methyl-6-(4-pyridinyl)-3(2H)-pyridazinone.
A-21. 2-(n-Butyl)-4,5-dihydro-4-methyl-6-(4-pyridinyl)-3(2H)-pyridazinone.
A-22. 2-Ethyl-6-(3-ethyl-4-pyridinyl)-4,5-dihydro-4-methyl-3(2H)-pyridazinone.
A-23. 4,5-Dihydro-2-(2-hydroxyethyl)-4-methyl-6-(4-pyridinyl)-3(2H)-pyridazinone.

Following the procedure described in Example A-16 but using in place of methyl 4-cyano-4-(4-morpholinyl)-4-(4-pyridinyl)-2-methylbutanoate a molar equivalent quantity of methyl 2-methyl-4-oxo-4-(4-pyridinyl)-butanoate, it is contemplated that there can be obtained 4,5-dihydro-2,4-dimethyl-6-(4-pyridinyl)-3(2H)-pyridazinone. Also, this same compound can be obtained following the procedure described in Example A-1 but using in place of 4-oxo-4-(4-pyridinyl)butanenitrile a molar equivalent quantity of 2-methyl-4-oxo-4-(4-pyridinyl)butanenitrile.

B. 2-R-4-R'-6-PY-3(2H)-PYRIDAZINONES

[These compounds where R' is hydrogen and their preparation are disclosed and claimed in said copending application Ser. No. 144,576, filed Apr. 28, 1980.]

B-1. 2-Methyl-6-(4-pyridinyl)-3(2H)-pyridazinone

To a warm solution containing 28 g. of 4,5-dihydro-2-methyl-6-(4-pyridinyl)-3(2H)-pyridazinone monohydrochloride and 140 ml. of acetic acid was added with stirring 100 ml. of bromine, and the resulting reaction mixture was refluxed overnight and then allowed to cool to room temperature. The solid that had separated was collected, stirred with 150 ml. of water and to the aqueous mixture was added sodium bisulfite until bubbling ceased. To the resulting pale yellow solution was added sufficient solid sodium bicarbonate to make it mildly basic to litmus and the resulting mixture was extracted with chloroform. The chloroform extract was heated in vacuo to remove the solvent and the resulting solid was recrystallized from methanol-ether and dried in a vacuum oven at 60° C. overnight to yield 15 g. of 2-methyl-6-(4-pyridinyl)-3(2H)-pyridazinone, m.p. 175°–185° C.

Acid-addition salts of 2-methyl-6-(4-pyridinyl)-3(2H)-pyridazinone are conveniently prepared by adding to a mixture of 1 g. of 2-methyl-6-(4-pyridinyl)-3(2H)-pyridazinone in about 20 ml of aqueous methanol the appropriate acid, e.g., hydrochloric acid, methanesulfonic acid, sulfuric acid, to a pH of about 2 to 3, chilling the mixture after partial evaporation and collecting the precipitated salt, e.g., hydrochloride, methanesulfonate, sulfate, respectively. Also, the lactate or hydrochloride acid-addition salt of 2-methyl-6-(4-pyridinyl)-3(2H)-pyridazinone is conveniently prepared in aqueous solution by adding to water with stirring molar equivalent quantities each of 2-methyl-6-(4-pyridinyl)-3(2H)-pyridazinone and lactic acid or hydrochloric acid, respectively.

Following the procedure described in Example B-1 but using in place of 4,5-dihydro-2-methyl-6-(4-pyridinyl)-3(2H)-pyridazinone or monohydrochloride thereof a corresponding molar equivalent quantity of the appropriate 4,5-dihydro-2-R-4-R'-6-PY-pyridazinone or monohydrochloride salt thereof, it is contemplated that the corresponding 2-R-4-R'-6-PY-3(2H)-pyridazinones of Examples B-2 thru B-23 can be obtained.

B-2. 2-Ethyl-6-(4-pyridinyl)-3(2H)-pyridazinone.
B-3. 2-Isopropyl-6-(4-pyridinyl)-3(2H)-pyridazinone.
B-4. 2-n-Propyl-6-(4-pyridinyl)-3(2H)-pyridazinone.
B-5. 2-Isobutyl-6-(4-pyridinyl)-3(2H)-pyridazinone.
B-6. 2n-Hexyl-6-(4-pyridinyl)-3(2H)-pyridazinone.
B-7. 2-(2-Hydroxyethyl)-6-(4-pyridinyl)-3(2H)-pyridazinone.
B-8. 2-(2-Hydroxypropyl)-6-(4-pyridinyl)-3(2H)-pyridazinone.
B-9. 2-(3-Hydroxypropyl)-6-(4-pyridinyl)-3(2H)-pyridazinone.
B-10. 2-(4-Hydroxybutyl)-6-(4-pyridinyl)-3(2H)-pyridazinone.
B-11. 2-Methyl-6-(3-pyridinyl)-3(2H)-pyridazinone.
B-12. 2-Methyl-6-(2-methyl-3-pyridinyl)-3(2H)-pyridazinone.
B-13. 2-Methyl-6-(5-methyl-3-pyridinyl)-3(2H)-pyridazinone.
B-14. 6-(3-Ethyl-4-pyridinyl)-2-methyl-3(2H)-pyridazinone.
B-15. 2-Methyl-6-(2,6-dimethyl-4-pyridinyl)-3(1H)-pyridazinone.
B-16. 2,4-Dimethyl-6-(4-pyridinyl)-3(2H)-pyridazinone.
B-17. 2,4-Dimethyl-6-(3-pyridinyl)-3(2H)-pyridazinone.
B-18. 2-Ethyl-4-methyl-6-(4-pyridinyl)-3(2H)-pyridazinone.
B-19. 4-Methyl-2-n-propyl-6-(4-pyridinyl)-3(2H)-pyridazinone.
B-20. 2-Isopropyl-4-methyl-6-(4-pyridinyl)-3(2H)-pyridazinone.
B-21. 2-(n-Butyl)-4-methyl-6-(4-pyridinyl)-3(2H)-pyridazinone.
B-22. 2-Ethyl-6-(3-ethyl-4-pyridinyl)-4-methyl-3(2H)-pyridazinone.
B-23. 2-(2-Hydroxyethyl)-4-methyl-6-(4-pyridinyl)-3(2H)-pyridazinone.

C. 4-OXO-4-PY-BUTANENITRILES

C-1. 4-Oxo-4-(4-pyridinyl)butanenitrile

To a stirred mixture containing 29.4 g. of sodium cyanide and 500 ml. of acetonitrile, after stirring said mixture for ten minutes, was added dropwise over a period of three hours a solution containing 64.2 g. of 4-pyridinecarboxaldehyde in 500 ml of acetonitrile and the resulting mixture was stirred at room temperature for one hour. To the stirred mixture was added slowly over a period of one hour a solution of 24.5 g. of acrylonitrile in 200 ml. of acetonitrile and the resulting reaction mixture was stirred overnight at room temperature. The reaction mixture was stripped in vacuo of solvent at a temperature not exceeding 54° C. The semi-solid residue was cooled, mixed well with 400 ml of chloroform, and the mixture filtered. The chloroform was distilled off in vacuo at a temperature not exceeding 50° C. and the residual oily residue was extracted with three 200 ml. portions of toluene. The toluene solution was filtered through diatomaceous earth and the filtrate was distilled in vacuo below 50° C. to remove the toluene. The residue on chilling crystallized. A tiny sample was saved and the remainder was dissolved in 50 ml. of warm isopropyl alcohol. The solution was cooled and then diluted slowly with 125 ml. of ether, chilled and seeded with a crystal obtained from said tiny sample. The crystalline product that separated was collected, washed with 25 ml. of 1:3 (v:v) mixture of isopropyl alochol:ether, and air dried to yield 52.1 g. of 4-oxo-4-(4-pyridinyl)butanenitrile, m.p. 53.5°–55° C.

Following the procedure described in Example C-1 but using in place of 4-pyridinecarboxaldehyde a molar equivalent quantity of the appropriate 4- or 3-PY-carboxaldehyde, it is contemplated that there can be obtained the corresponding 4-oxo-4-PY-butanenitriles of Examples C-2 thru C-6, respectively.

C-2. 4-Oxo-4-(3-pyridinyl)butanenitrile.
C-3. 4-(2-Methyl-3-pyridinyl)-4-oxobutanenitrile.
C-4. 4-(5-Methyl-3-pyridinyl)-4-oxobutanenitrile.
C-5. 4-(3-Ethyl-4-pyridinyl)-4-oxobutanenitrile.
C-6. 4-(2,6-Dimethyl-4-pyridinyl)-4-oxobutanenitrile.

Following the procedure described in Example C-1 but using in place of acrylonitrile a molar equivalent quantity of methacrylonitrile, it is contemplated that their can be obtained the corresponding compound of Example C-7.

C-7. 2-Methyl-4-oxo-4-(4-pyridinyl)butanenitrile.

D. LOWER-ALKYL 4-(BN)-4-CYANO-4-PY-2-R'-BUTANOATES

D-1. Methyl 4-Cyano-2-methyl-4-(4-morpholinyl)4-(4-pyridinyl)-butanoate

To a mixture containing 16 g. of 2-(4-morpholinyl)-2-(4-pyridinyl)ethanenitrile and 150 ml. of tetrahydrofuran in a flask equipped with a stirrer and drying tube was added with stirring 6 ml of 30% potassium hydroxide in methanol, followed by 8.5 g. of methyl methacrylate. Within thirty minutes an exothermic reaction ensued and a white solid began to separate. The reaction mixture was stirred for one hour and then allowed to stand at room temperature overnight. The reaction mixture was concentrated by heating in vacuo to remove solvent and the remaining residue was triturated with absolute ether (about 600 ml.) and filtered. The filtrate was concentrated to a volume of about 50 ml., cooled, treated with 50 ml. of n-hexane and chilled. The product that separated was collected and dried at 70° C. to yield 11 g. of methyl 4-cyano-2-methyl-4-(4-morpholinyl)-4-(4-pyridinyl)butanoate, m.p. 93°–94° C.

Acid-addition salts of methyl 4-cyano-2-methyl-4-(4-morpholinyl)-4-(4-pyridinyl)butanoate are conveniently prepared by adding to a mixture of 1 g. of methyl 4-cyano-2-methyl-4-(4-morpholinyl)-4-(4-pyridinyl)-butanoate in about 20 ml. of aqueous methanol the appropriate acid, e.g., hydrochloric acid, methanesulfonic acid, sulfuric acid, to a pH of about 2 to 3, chilling the mixture after partial evaporation and collecting the precipitated salt, e.g., hydrochloride, methanesulfonate, sulfate, respectively. Also, the lactate or hydrochloride acid addition salt of methyl 4-cyano-2-methyl 4-(4-morpholinyl)-4-(4-pyridinyl)butanoate is conveniently prepared in aqueous solution by adding to water with stirring molar equivalent quantities each of methyl 4-cyano-2-methyl-4-(4-morpholinyl)-4-(4-pyridinyl)-butanoate and lactic acid or hydrochloric acid, respectively.

Following the procedure described in Example D-1 but using in place of 2-(4-morpholinyl)-2-(4-pyridinyl)ethanenitrile and methyl methacrylate molar equivalent quantities respectively of the appropriate 2-(BN)-2-PY-ethanenitrile and lower-alkyl methacrylate, it is contemplated that there can be obtained the corresponding lower-alkyl 4-cyano-2-methyl-4-(BN)-4-PY-butanoates of Examples D-2 through D-6.

D-2. Methyl 4-cyano-2-methyl-4-(1-piperidinyl)-4-(4-pyridinyl)butanoate.

D-3. Methyl 4-cyano-2-methyl-4-(4-pyridinyl)-4-(1-pyrrolidinyl)butanoate.

D-4. Methyl 4-cyano-2-methyl-4-(4-morpholinyl)-4-(3-pyridinyl)butanoate.

D-5. Ethyl 4-cyano-2-methyl-4-(4-morpholinyl)-4-(4-pyridinyl)butanoate.

D-6. n-Propyl 4-cyano-4-(3-ethyl-4-pyridinyl)-2-methyl-4-(4-morpholinyl)butanoate.

E. 2-(BN)-2-PY-ETHANENITRILES

These generally known intermediates can be prepared by reacting a cyclic amine of the formula BN-H and an alkali cyanide with a PY-aldehydebisulfite complex according to Janssen et al [J. Am. Pharm. Assoc., Sci. Ed. 44, 465–7 (1955)] or by the following alternative procedure described in Example E-1.

E-1. 2-(4-Morpholinyl)-2-(4-pyridinyl)ethanenitrile

A mixture containing 72 g. of 4-pyridinecarboxaldehyde, 140 g. of morpholine, 152 g. of p-toluenesulfonic acid and 800 ml. of tetrahydrofuran was refluxed with stirring for two hours and then allowed to cool to room temperature. To the stirred reaction mixture was added 64 g. of potassium cyanide in 20 ml. of water and the resulting reaction mixture was refluxed for two hours and allowed to stand overnight at room temperature. The reaction mixture was filtered and the filtrate was heated in vacuo to remove the solvent. To the resulting gummy residue was added about 800 ml. of chloroform and about 300 ml of saturated sodium chloride solution. The mixture was stirred for two hours and filtered. The heterogeneous filtrate was transferred to a separatory funnel, shaken well, and the chloroform layer drained off and heated in vacuo to remove the chloroform. The residue was boiled with about 300 ml. of water, chilled and seeded whereupon pale yellow crystals separated. The filtrate was concentrated in vacuo to a volume of about 60 ml. and a second crop of pale yellow crystals was obtained. The combined crops of yellow crystals were dried first in a vacuum oven at 100 mm. and 25° C., and then for 100 hours over $P_2O_5$ to yield 40 g. of 2-(4-morpholinyl)-2-(4-pyridinyl)ethanenitrile, m.p. 64°–65° C.

Following the procedure described in Example E-1 using a molar equivalent quantities of the respective appropriate pyridinecarboxaldehyde and amine (BN-H) in place of 4-pyridinecarboxyaldehyde and morpholine, it is contemplated that there can be obtained and corresponding 2-(BN)-2-PY-ethanenitriles of Examples E-2 through E-5.

E-2. 2-(4-Pyridinyl)-2-(1-pyrrolidinyl)ethanenitrile.

E-3. 2-(1-Piperidinyl)-2-(4-pyridinyl)ethanenitrile.

E-4. 2-(3-Ethyl-4-pyridinyl)-2-(4-morpholinyl)ethanenitrile.

E-5. 2-(5-Methyl-3-pyridinyl)-2-(4-morpholinyl)ethanenitrile.

The usefulness of the compounds of formula I or salts thereof as cardiotonic agents is demonstrated by their effectiveness in standard pharmacological test procedures, for example, in causing a significant increase in contractile force of the isolated cat atria and papillary muscle and in causing a significant increase in the cardiac contractile force in the anesthetized dog with low or minimal changes in heart rate and blood pressure. Detailed descriptions of these test procedures appear in U.S. Pat. No. 4,072,746, issued Feb. 7, 1980.

When tested by said isolated cat atria and papillary muscle procedure, the compounds of formula I or pharmaceutically-acceptable acid-addition salts thereof at doses of 10, 30, 100 and/or 300 µg/ml. were found to cause significant increases, that is, greater than 25% in papillary muscle force and significant increases, that is, greater than 25%, in right atrial force, while causing a lower percentage increase (about one-third or less than the percentage increase in right atrial force or papillary muscle force) in right atrial rate. For example, when tested at dose levels of 10, 30 and 100 µg/ml. by this procedure, the compound of Example A-1, i.e., 4,5-dihydro-2-methyl-6-(4-pyridinyl)-3(2H)-pyridazinone as its monohydrochloride, was found to cause increases of 35% to 77% in papillary muscle force and/or right atrial force; when tested at 100 µg/ml. by the comparable test procedure using isolated guinea pig atria and papillary muscle, the compound of Example A-16, i.e. 4,5-dihydro-2,4-dimethyl-6-(4-pyridinyl)-3(2H)-pyridazinone, was found to cause respective increases of 75% and 63% in papillary muscle force and right atrial force.

The present invention includes within its scope a cardiotonic composition for increasing cardiac contractility, said composition comprising a pharmaceutically-acceptable carrier and, as the active component thereof, the cadiotonic compound of formula I or pharmaceutically-acceptable acid-addition salt thereof. The invention also includes within its scope the method for increasing cardiac contractility in a patient requiring such treatment which comprises administering to such patient a cardiotonically-effective amount of a compound of formula I or pharmaceutically-acceptable acid-addition salt thereof. In clinical practice said compound or salt thereof will normally be administered orally or parenterally in a wide variety of dosage forms.

Solid compositions for oral administration include compressed tablets, pills, powders and granules. In such solid compositions, at least one of the active compounds is admixed with at least one inert diluent such as starch, calcium carbonate, sucrose or lactose. These compositions can also contain additional substances other than inert diluents, e.g., lubricating agents, such as magnesium stearate, talc and the like.

Preparations according to the invention for parenteral administration include sterile aqueous, aqueous-organic, and organic solutions, suspensions and emulsions. Examples of organic solvents or suspending media are propylene glycol, polyethylene glycol, vegetable oils such as olive oil and injectable organic esters such as ethyl oleate. These compositions can also contain adjuvants such as stabilising, preserving, wetting, emulsifying and dispersing agents.

They can be sterilized, for example, by filtration through a bacteria-retaining filter, by incorporation of sterilising agents in the compositions, by irradiation or by heating. They can also be manufactured in the form of sterile solid compositions which can be dissolved in sterile water or some other sterile injectable medium immediately before use.

The percentages of active component in the said composition and method for increasing cardiac contractility can be varied so that a suitable dosage is obtained. The dosage administered to a particular patient is variable, depending upon the clinician's judgement using as the criteria: the route of administration, the duration of treatment, the size and condition of the patient, the potency of the active component and the patient's response thereto. An effective dosage amount of active component can thus only be determined by the clinician considering all criteria and utilizing the best judgement on the patient's behalf.

We claim:

1. 4,5-Dihydro-2-methyl-6-(4-pyridinyl)-3(2H)-pyridazinone or pharmaceutically-acceptable acid-addition salt there.

2. A cardiotonic composition for increasing cardiac contractility, said composition comprising a pharmaceutically-acceptable inert carrier and, as the active component thereof, a cardiotonically-effective amount of 4,5-dihydro-2-methyl-6-(4-pyridinyl)-3(2H)-pyridazinone or pharmaceutically-acceptable acid-addition salt thereof.

3. The method for increasing cardiac contractility in a patient requiring such treatment which comprises administering orally or parenterally in a solid or liquid dosage form to such patient a cardiotonically-effective amount of 4,5-dihydro-2-methyl-6-(4-pyridinyl)-3(2H)-pyridazinone or pharmaceutically-acceptable acid-addition salt thereof.

* * * * *

UNITED STATES PATENT AND TRADEMARK OFFICE
CERTIFICATE OF CORRECTION

PATENT NO. : 4,337,253
DATED : June 29, 1982
INVENTOR(S) : George Y. Lesher et al.

It is certified that error appears in the above-identified patent and that said Letters Patent are hereby corrected as shown below:

Column 12, line 56, "cadiotonic" should read -- cardiotonic --.

Claim 1, line 3, "there" should read -- thereof --.

Signed and Sealed this

Fifteenth Day of March 1983

[SEAL]

Attest:

GERALD J. MOSSINGHOFF

Attesting Officer      Commissioner of Patents and Trademarks